United States Patent [19]
Nakao

[11] Patent Number: 5,458,582
[45] Date of Patent: Oct. 17, 1995

[54] POSTOPERATIVE ANESTHETIC DELIVERY DEVICE AND ASSOCIATED METHOD FOR THE POSTOPERATIVE TREATMENT OF PAIN

[76] Inventor: Naomi L. Nakao, 303 E. 57th St., New York, N.Y. 10022

[21] Appl. No.: 898,510

[22] Filed: Jun. 15, 1992

[51] Int. Cl.$^6$ .................................................. A61M 25/00
[52] U.S. Cl. ........................................................ 604/264
[58] Field of Search ..................... 604/258, 65–67, 604/264, 280–284; 623/12; 606/191–194

[56] References Cited

U.S. PATENT DOCUMENTS

| | | | |
|---|---|---|---|
| 1,236,865 | 8/1917 | Pittenger | 604/258 |
| 2,593,980 | 4/1952 | Calicchio | 604/265 |
| 2,624,341 | 7/1953 | Wallace | 604/284 |
| 3,064,653 | 11/1962 | Coanda | 604/280 |
| 4,072,153 | 2/1978 | Swartz | 604/284 |
| 4,692,153 | 9/1987 | Berlin et al. | 604/280 |
| 4,784,638 | 11/1988 | Ghajar et al. | 604/264 |
| 4,846,792 | 7/1989 | Bobo, Jr. et al. | 128/DIG. 13 |
| 4,846,812 | 7/1989 | Walker et al. | 604/265 |
| 4,898,578 | 2/1990 | Rubalcoba, Jr. | 128/DIG. 13 |
| 4,925,452 | 5/1990 | Melingshyn et al. | 604/284 |
| 4,961,731 | 10/1990 | Bodicky et al. | 604/264 |
| 5,156,597 | 10/1992 | Verret et al. | 604/286 |
| 5,186,711 | 2/1993 | Epstein | 623/12 |

*Primary Examiner*—John D. Yasko
*Assistant Examiner*—Manuel Mendez
*Attorney, Agent, or Firm*—Davis Hoxie Faithfull & Hapgood

[57] ABSTRACT

An anesthesia delivery device comprising an elongate flexible tubular member in the form of a hollow suture made of bioabsorbable material, the tubular member having a proximal end portion with a continuous cylindrical side wall and a distal end portion provided with a plurality of apertures spaced longitudinally along the distal end portion. The delivery device further comprises an injection pump or other component connected to the proximal end portion of the tubular member for injecting a local anesthetic into the tubular member. A timer can be provided for determining a time for an injection of the local anesthetic into a patient in which the distal end portion of the tubular member is implanted.

4 Claims, 2 Drawing Sheets

POSTOPERATIVE ANESTHETIC DELIVERY DEVICE AND ASSOCIATED METHOD FOR THE POSTOPERATIVE TREATMENT OF PAIN

BACKGROUND OF THE INVENTION

This invention relates to a device or system for the delivery and, more particularly, postoperative delivery, of local anesthesia to an operative site in a patient. This invention also relates to an associated method for the postoperative treatment of pain.

In conventional surgery, for example, surgery involving the removal of cancerous tissues, a local anesthetic is injected or otherwise applied to the operative site prior to incision closure. Such a local anesthetic is effective for at most approximately six hours. Thereafter, the patient must be given morphine or another drug which acts on the central nervous system for easing the inevitable pain. Morphine and the other drugs used for this purpose have many undesirable side effects including, for example, a loss of alertness, difficulty in breathing, interference with even simple daily movement, nausea, and, in some cases, possible addiction. Some patients suffer such post operative pain that proper breathing is inhibited, requiring respiratory therapy and often resulting in pneumonia.

OBJECTS OF THE INVENTION

An object of the present invention is to provide a method and/or a device for the postoperative treatment of pain.

Another object of the present invention is to provide such a method and/or device which reduces, if not eliminates, at least some of the undesirable side effects due to the use of pain killers which act on the central nervous system.

Another, more particular, object of the present invention is to provide such a method which is easy to implement.

A further particular object of the present invention is to provide such a device which is inexpensive.

Yet another particular object of the present invention is to provide a method and/or a device for the postoperative treatment of pain wherein anesthesia effects are generally limited to the surgical site.

Other objects of the present invention will be apparent from the detailed descriptions and drawings included herein.

SUMMARY OF THE INVENTION

An anesthesia delivery device comprises, in accordance with the present invention, an elongate flexible tubular member made of bioabsorbable material, the tubular member having a proximal end portion with a continuous side wall and a distal end portion provided with a plurality of apertures spaced longitudinally along the distal end portion.

Pursuant to another feature of the present invention, the delivery device further comprises an injection component connected to the proximal end portion of the tubular member for injecting a local anesthetic into the tubular member. The interior of the delivery device is maintained in a substantially aseptic condition during use. More particularly, the injection component includes a pump or other unit for automatically injecting an aliquot of the local anesthetic into the tubular member. In that event, a timer is advantageously provided for determining the time for an injection of the local anesthetic into a patient in which the distal end portion of the tubular member is implanted.

Preferably, the tubular member has a diameter approximately equal to that of a suture thread. The tubular member is thus a bioabsorbable hollow suture thread with a plurality of interspaced apertures in a sidewall of the distal end portion of the tubular member.

According to another feature of the present invention, the distal end portion of the tubular member includes a plurality of branches, each of the branches being provided with a plurality of apertures spaced longitudinally along the respective branch.

A method for the postoperative treatment of pain comprises, in accordance with the present invention, the steps of (a) providing an elongate flexible tubular member made of bioabsorbable material, the tubular member having a proximal end portion with a continuous side wall and a distal end portion provided with a plurality of apertures spaced longitudinally along the distal end portion, (b) prior to the closing of an incision in a patient during a surgical procedure, laying the distal end portion of the tubular member into the patient, preferably at various levels of the incision (i.e., between the muscles and organs, under the skin, etc. wherever the source of post-operative pain lies), (c) closing the incision with the proximal end portion extending outside of the patient through the incision closure, and (d) upon the closure of the incision, periodically delivering a local anesthetic into the tubular member via the proximal end portion.

Pursuant to another feature of the present invention, the step of anesthesia delivery is implemented automatically. More particularly, an aliquot of the local anesthetic is automatically pumped into the tubular member.

Where the distal end portion of the tubular member includes a plurality of branches, each of the branches being provided with a plurality of apertures spaced longitudinally along the respective branch, the method further comprises the step of arranging the branches along different contours of an operative site. Alternatively or additionally, the branches are arranged to be disposed in different types of organic tissues. For example, one branch can be disposed adjacent an internal organ, while another branch is disposed in overlying muscle tissues and yet another branch in subcutaneous tissues.

Alternatively, several separate tubular anesthetic delivery devices can be used during a surgical closure procedure, each tubular member being disposed in a different type of tissue. A first such tubular member to be used is longer and has a perforated distal end portion disposed adjacent an internal organ. A second such tubular member is disposed in overlying muscle tissues and another tubular member in subcutaneous tissues. The subcutaneous tubular anesthetic delivery device is the shortest.

This last alternative allows for the injection of different anesthetics into the different tissues or for injections at different rates. In addition, the bioabsorbability of the different tubular members can be varied to accord with the different tissue types and with different kinds of operations.

A method or a device for the postoperative treatment of pain in accordance with the present invention reduces, if not eliminates, at least some of the undesirable side effects due to the use of pain-killer drugs which act on the central nervous system. More particularly, because anesthesia can be limited to local anesthesia, the complications and side effects from the utilization of drugs acting on the central nervous system are avoided.

A method in accordance with the present invention is easy to implement. The suture-like delivery tubes need only be laid in place during the closure procedure. Injection of the anesthetic can be done with conventional hypodermic syringes. Alternatively, in accordance with the present invention, the injection may be implemented automatically, according to a predetermined regimen. The latter embodiment of the invention is especially useful in the case of ambulatory patients. The tubular member, anesthesia and pump must be maintained in a substantially aseptic condition during use so that no infection reaches the tissue to be anesthetized. The interior of the tubular member should be maintained in an air-tight condition such that microorganisms external to patent do not invade the tubular member and infect the patient.

A device in accordance with the present invention is inexpensive, hardly more expensive than a conventional suture.

DETAILED DESCRIPTION

Figure 1:
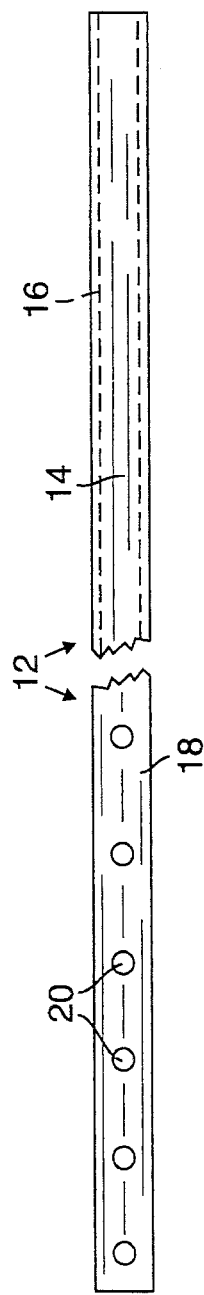
FIG. 1 is a schematic side elevational view of a postoperative anesthetic delivery device in accordance with the present invention.

As illustrated in FIG. 1, a postoperative anesthesia delivery device comprises an elongate flexible tubular member 12 made of bioabsorbable material. Tubular member 12 has a proximal end portion 14 with a continuous cylindrical side wall 16 and a distal end portion 18 provided with a plurality of apertures or perforations 20 spaced longitudinally along distal end portion 18.

The postoperative anesthesia delivery device further comprises an injection component such as a conventional hypodermic syringe 22 (FIG. 4) connectable to proximal end portion 14 for injecting a local anesthetic into tubular member 12. Alternatively, a bag (not shown) filled with local anesthetic may be connected to proximal end 18. Compressing the bag would force anesthetic to flow through the tubular member 12 to the tissue.

Figure 2:
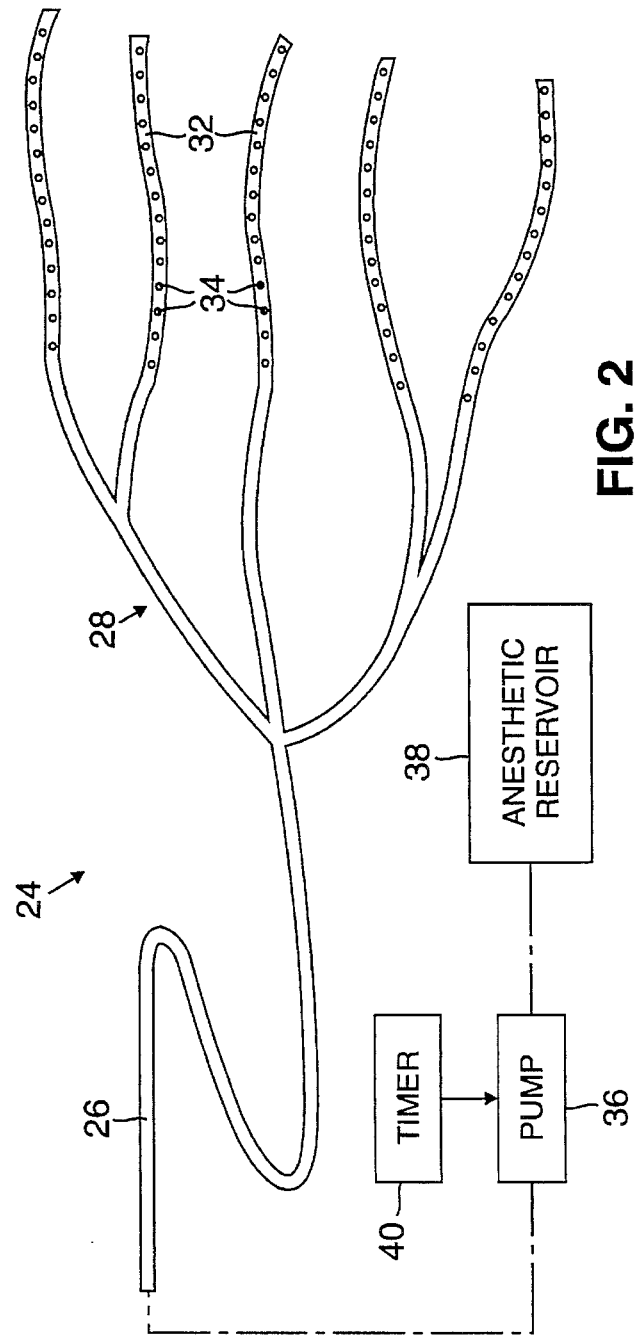
FIG. 2 is a schematic perspective view of another postoperative anesthetic delivery device in accordance with the present invention.

As illustrated in FIG. 2, another postoperative anesthesia delivery device comprises an elongate flexible tubular member 24 made of bioabsorbable material. Tubular member 24 has a proximal end portion 26 with a continuous cylindrical side wall and a distal end portion 28 formed with a plurality of branches 32 each provided with a plurality of apertures or perforations 34 spaced longitudinally along the respective distal end branch 32.

The postoperative anesthesia delivery device further comprises an automatic injection component in the form of a pump 36 connected to proximal end portion 26 for injecting into tubular member 24 a local anesthetic from a reservoir or storage tank 38. A timer 40 is operatively connected to a control input (not designated) of pump 36 for determining successive times for an injection of the local anesthetic into a patient in which distal end portion 28 of tubular member 24 is implanted. Pump 36, reservoir 38 and timer 40 can be housed in a common casing (not shown) and attached to the patient via a belt (not shown) or other fastener. The casing interior should be aseptic to prevent any infection from reaching the tissue via the tubular member 24.

Tubular members 12 and 24 can each have a diameter approximately equal to that of a suture thread.

In a method for the postoperative treatment of pain utilizing tubular member 12 or 14, distal end portion 18 or 28 of the tubular member is laid into the patient prior to the closing of a surgical incision. The incision is subsequently closed with proximal end portion 14 or 26 extending outside of the patient through the incision closure. Upon closure of the incision, a local anesthetic is periodically delivered into tubular member 12 or 24 via proximal end portion 14 or 26. The delivery of the anesthetic can be implemented manually, e.g., through the use of syringe 22 (FIG. 4) or automatically, e.g., through the operation of pump 36 under the control of timer 40.

Figure 3:
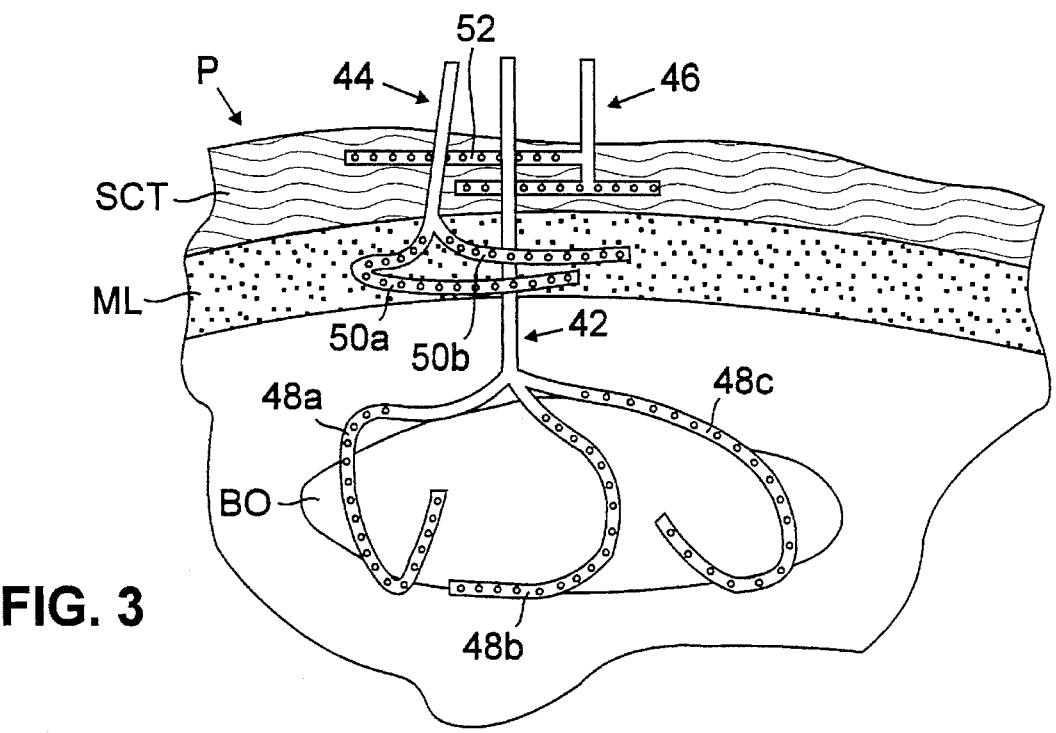
FIG. 3 is a schematic cross-sectional view through a patient, illustrating use of a plurality of postoperative anesthetic delivery devices in accordance with the present invention.

FIG. 3 is a schematic cross-sectional view through a patient P, illustrating use of three perforated flexible tubular postoperative anesthetic delivery devices 42, 44 and 46. Upon the termination of surgery on or about an internal body organ BO, postoperative anesthesia delivery device 42 is inserted through an incision and manipulated to arrange branches 48a, 48b and 48c about organ BO. During closure of an overlying muscle layer ML, branches 50a and 50b of postoperative anesthesia delivery device 44 are laid inside the muscle tissues of layer ML. Subsequently, a distal end portion 52 of postoperative anesthesia delivery device 46 is disposed inside subcutaneous connective tissues SCT.

Postoperative anesthesia delivery devices 42, 44 and 46 can have different lengths, with delivery device 42 being the longest and delivery device 46 being the shortest. The utilization of several different postoperative anesthesia delivery devices 42, 44 and 46, with their respective proximal end portions outside of the patient, allows for the injection of different anesthetics and/or different amounts of anesthetics into the different tissues BO, ML and SCT or for injections at different rates or different times. In addition, the bioabsorbability of postoperative anesthesia delivery devices 42, 44 and 46 can be varied to accord with the different tissue types and with different kinds of operations.

Where the distal end portion of the tubular member includes a plurality of branches, each of the branches being provided with a plurality of apertures spaced longitudinally along the respective branch, the method further comprises the step of arranging the branches along different contours of an operative site. Alternatively or additionally, the branches are arranged to be disposed in different types of organic tissues. For example, one branch can be disposed adjacent an internal organ, while another branch is disposed in overlying muscle tissues and yet another branch in subcutaneous tissues.

Figure 4:
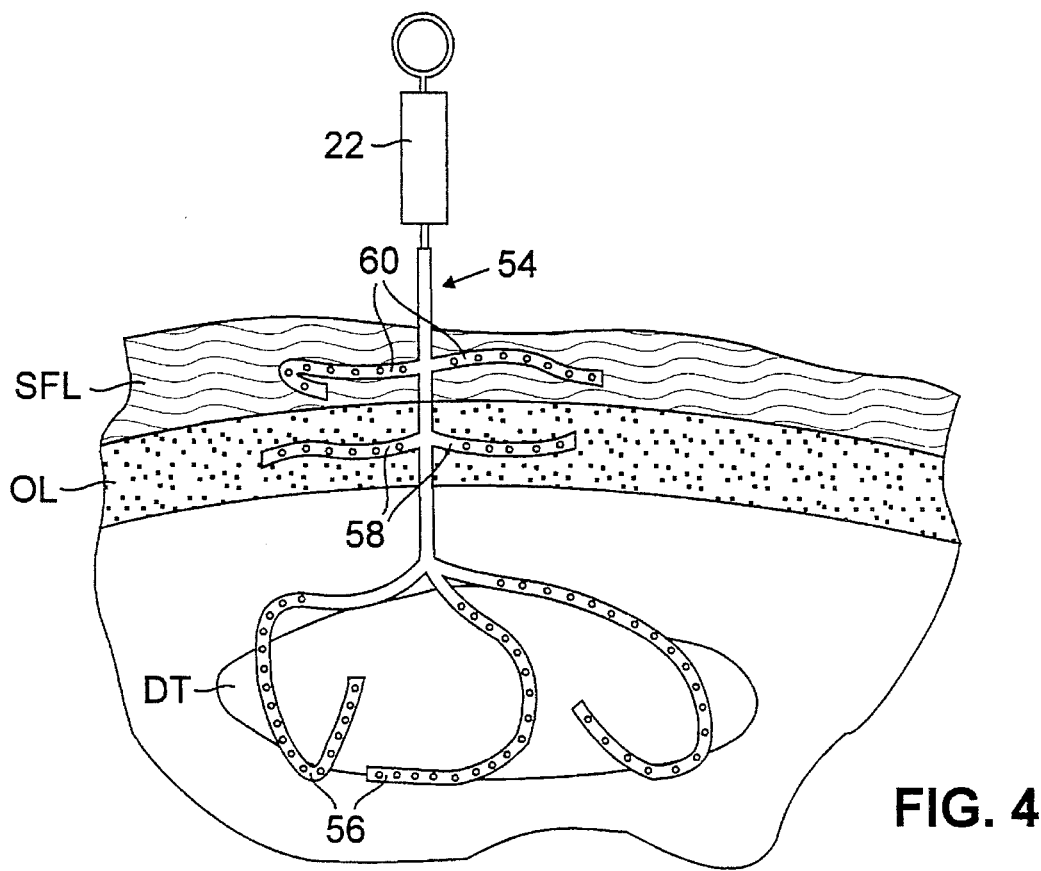
FIG. 4 is another schematic cross-sectional view through a patient, illustrating use of an additional postoperative anesthetic delivery device in accordance with the present invention.

FIG. 4 illustrates use of a single postoperative anesthesia delivery device 54 having three levels of branches 56, 58 and 60 for disposition about an internal organ or deep tissues DT, an overlying layer of muscle tissue OL and an outer layer of subcutaneous fat SFL.

Although the invention has been described in terms of particular embodiments and applications, one of ordinary skill in the art, in light of this teaching, can generate additional embodiments and modifications without departing from the spirit of or exceeding the scope of the claimed invention. For example, a hollow tubular postoperative anesthesia delivery device can have virtually any number and organization of branches. The perforations or outlet apertures in the distal ends of the branches can have different sizes and distributions to control the rate and amount of anesthetic delivered to different tissues at a surgical site within a patient. The distal tips can be closed to better enable the distribution of fluidic anesthetic through apertures along the sidewall of a postoperative anesthesia delivery device.

It is to be noted that bioabsorbable materials for sutures are well known and would work with the instant invention. Within two or three weeks of implantation, a postoperative anesthesia delivery device in accordance with the present invention is absorbed in the body. External threads, i.e., the proximal ends of partially implanted postoperative anesthesia delivery devices, may be pulled out upon disintegration of the implanted distal end portions of the respective postoperative anesthesia delivery devices. The postoperative anesthesia delivery devices remain intact long enough for the effective application of local anesthesia to a patient.

Accordingly, it is to be understood that the drawings and descriptions herein are proffered by way of example to facilitate comprehension of the invention and should not be construed to limit the scope thereof.

What is claimed is:

1. Anesthesia supply means for post-operatively supplying anesthesia to the interior of a surgical wound along at least one line of sutures joining tissue at the source of the post-operative pain in the interior of the wound, the site of the surgical wound being closed following surgery, the supply means comprising an elongate flexible tubular member made of bioabsorable material, said tubular member having a proximal end portion with a continuous side wall and adapted to project from the closed wound, and a distal end portion for laying along one or more lines of sutures joining tissue closing the interior of the wound, said distal end portion comprised of at least one tubular member provided with a plurality of anesthesia discharge apertures spaced longitudinally along said distal end portion.

2. The anesthetic supply means of claim 1 wherein said distal end portion of said tubular member includes a plurality of branches, each of said branches being provided with a plurality of apertures spaced longitudinally along the respective branch.

3. Anesthesia supply means for post-operatively supplying anesthesia to the interior of a surgical wound along at least one line of sutures joining tissue at the source of the post-operative pain in the interior of the wound, the site of the surgical wound being closed following surgery, the supply means comprising an elongate flexible tubular member made of bioabsorabable material, said tubular member having a proximal end portion with a continuous side wall and a distal end portion for laying along one or more lines of sutures joining tissue closing the interior of the wound, said distal end portion provided with a plurality of anesthesia discharge apertures spaced longitudinally along said distal end portion, said tubular member having a diameter approximately equal to that of a suture thread, said distal end portion of said tubular member including a plurality of branches, each of said branches being provided with a plurality of anesthesia discharge apertures spaced longitudinally along the respective branch, further comprising means connected to said proximal end portion for injecting a local anesthetic into said tubular member.

4. The anesthetic supply means of claim 3 wherein said means for automatically injecting includes timing means for determining a time for an injection of said local anesthetic into a patient in which said distal end portion is implanted, said means for automatically injecting further including pumping means connected to said timing means for pumping said aliquot of said local anesthetic into said tubular member in response to a signal from said timing means.

* * * * *